United States Patent
Ferritto et al.

(10) Patent No.: US 6,294,634 B1
(45) Date of Patent: Sep. 25, 2001

(54) ORGANOSILICON COMPOSITIONS FROM CYCLOSILOXANES

(75) Inventors: Michael Salvatore Ferritto; William James Schulz, Jr., both of Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/536,141

(22) Filed: Mar. 28, 2000

(51) Int. Cl.$^7$ .................................................... C08G 77/08
(52) U.S. Cl. .............................. 528/14; 528/33; 528/31; 528/37; 528/21; 528/23; 528/12; 556/445; 556/451
(58) Field of Search .................... 556/451, 445; 528/31, 33, 21, 23, 14, 12, 37

(56) References Cited

U.S. PATENT DOCUMENTS

| | | | |
|---|---|---|---|
| 2,868,766 | 1/1959 | Johannson | 260/46.5 |
| 2,994,684 | 8/1961 | Johannson | 260/46.5 |
| 3,002,951 | 10/1961 | Johannson | 260/46.5 |
| 3,299,112 | 1/1967 | Bailey | 260/448.2 |
| 3,427,271 | 2/1969 | McKellar | 260/29.2 |
| 4,532,132 * | 7/1985 | Keil | 514/772 |
| 4,810,305 | 3/1989 | Braun et al. | 106/499 |
| 5,160,494 | 11/1992 | Krzysik et al. | 512/3 |
| 5,344,906 | 9/1994 | Westall | 528/13 |
| 5,567,426 | 10/1996 | Nadaud et al. | 424/401 |
| 5,670,596 | 9/1997 | Razzano et al. | 528/16 |
| 5,830,969 | 11/1998 | Jallouli et al. | 528/21 |
| 5,883,215 | 3/1999 | Bischoff et al. | 528/21 |

OTHER PUBLICATIONS

Makromol. Chem., Macromol. Symp. "Anionic Ring Opening Polymerization of Cyclotetrasiloxanes With Large Substituents", vol. 32, pp. 241–253, 1990.

* cited by examiner

Primary Examiner—Margaret G. Moore
(74) Attorney, Agent, or Firm—James L. De Cesare

(57) ABSTRACT

A method of preparing organosilicon compositions by heating various mixtures of (i) dimethylcyclosiloxanes or methylhydrogencyclosiloxanes, (ii) homopolymeric and copolymeric cyclosiloxanes containing a C5 or more carbon atom containing group, and (iii) homopolymeric and copolymeric cyclosiloxanes containing an oxyalkylene segment, in the presence of a catalyst, at a temperature and for a time sufficient to cause polymerization of cyclosiloxanes (i) to (iii) to the desired organosilicon composition.

13 Claims, No Drawings

ORGANOSILICON COMPOSITIONS FROM CYCLOSILOXANES

BACKGROUND OF THE INVENTION

While Fish in Makromol. *Chem., Macromol. Symp.* 32, 241–253, (1990) in an article entitled "Anionic Ring Opening Polymerization of Cyclotetrasiloxanes with Large Substituents" suggests preparing organosilicon compositions by reacting octamethylcyclotetrasiloxane with either (i) a cyclosiloxane containing a higher carbon atom containing group, or (ii) a cyclosiloxane containing an oxyalkylene segment, Fish does not suggest preparing organosilicon compositions by reacting octamethylcyclotetrasiloxane with (i) a cyclosiloxane containing a higher carbon atom containing group and (ii) a cyclosiloxane containing an oxyalkylene segment.

Nor does Fish suggest preparing organosilicon compositions by reacting methylhydrogencyclosiloxanes with (i) cyclosiloxanes containing a higher carbon atom containing group and (ii) cyclosiloxanes containing an oxyalkylene segment.

Fish also does not suggest preparing organosilicon compositions by reacting octamethylcyclotetrasiloxane with (i) a copolymeric cyclosiloxane containing a higher carbon atom containing group, (ii) a copolymeric cyclosiloxane containing an oxyalkylene segment, or (iii) a copolymeric cyclosiloxane containing a higher carbon atom containing group, and a copolymeric cyclosiloxane containing an oxyalkylene segment.

BRIEF SUMMARY OF THE INVENTION

This invention relates to a method of preparing certain organosilicon compositions by heating various mixtures of (i) dimethylcyclosiloxanes or methylhydrogencyclosiloxanes, (ii) homopolymeric and copolymeric cyclosiloxanes containing a C5 or more, preferably a C8 or more, carbon atom containing group, and (iii) homopolymeric and copolymeric cyclosiloxanes containing an oxyalkylene segment, in the presence of a catalyst, at a temperature and for a time sufficient to cause polymerization of cyclosiloxanes (i) to (iii) to the desired organosilicon composition.

Organosilicon compositions containing dimethylsiloxane units, methyl oxyalkylene siloxane units, and methyl higher alkyl siloxane units, are known in the art, as evidenced by U.S. Pat. No. 3,427,271 (Feb. 11, 1969). However, the method for preparing such compositions requires a platinum catalyst. In contrast, the method according to the present invention does not require the use of platinum, and hence it offers an advantage and benefit in opening an avenue to organosilicon compositions that contain significantly reduced levels of residual platinum or to platinum-free organosilicon compositions, for use in consumer markets in which platinum has been determined to be an undesirable constituent, i.e., in personal care applications relating to hair, skin, and underarm.

These and other features and benefits of this invention will become apparent from a consideration of the detailed description.

BRIEF DESCRIPTION OF THE SEVERAL VIEWS OF THE DRAWING

Not applicable.

DETAILED DESCRIPTION OF THE INVENTION

Organosilicon compositions which can be prepared according to the method of this invention include compositions having the formula:

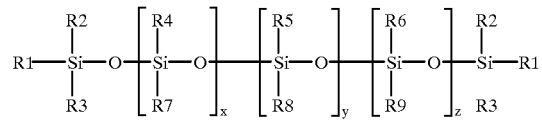

in which all of the groups R1 to R9 are hydrogen or an alkyl group containing 1–40 carbon atoms, preferably methyl, with the first proviso that R5 or R8 is a higher carbon atom containing group, i.e., a C5 or more, preferably a C8 or more group such as $-(CH_2)_7CH_3$, $-(CH_2)_{11}CH_3$, or $-(CH_2)_{15}CH_3$. The higher carbon atom containing group, therefore, should contain 5–40, preferably 8–40 carbon atoms. The second proviso is that R6 or R9 is a group containing an oxyalkylene segment represented by

If desired, R1 to R9 can also constitute an aryl group such as phenyl and xenyl (i.e., biphenyl); an aralkyl group such as benzyl, phenylethyl (i.e., phenethyl), and 2-phenylpropyl; an alkaryl group such as tolyl and xylyl; an haloalkyl group such as chloromethyl, 2-bromoethyl, 3-chloropropyl and 3,3,3-trifluoropropyl; an haloaryl group such as bromophenyl and chlorophenyl; an unsaturated alkenyl group such as vinyl, allyl, and hexenyl; or a substituted alkyl group such as acryloxypropyl, cyanopropyl, glycidoxypropyl, methacryloxypropyl, methoxypropyl, (methylthio)propyl, and ureidopropyl, for example; subject to the same provisos however, as noted above.

Q is a terminating radical which can be an alkyl group of one to six carbon atoms, an aryl group such as phenyl, an aralkyl group such as benzyl, an alkaryl group such as tolyl, or a trialkylsilyl group such as the trimethylsilyl group $-Si(CH_3)_3$. The value of a is 2–8, b is 4–60, and c is 0–60. The oxyalkylene segment preferably has 50–99.9 mole percent of oxyethylene units $-(C_2H_4O)_b$, and 0.1–50 mole percent of oxypropylene units $-(C_3H_6O)_c-$. Preferably, terminating radical Q is a methyl group; and a is three whereby the group $-C_aH_{2a}-$ is $-(CH_2)_3-$.

In the formula, x can have a value of 1 to 1,000; y can have a value of 0 to 1,000; and z can have a value of 0 to 1,000. Preferably, x, y, and z, are each 1 to 1,000; and all of the groups R1 to R9 are methyl, except for the higher carbon atom containing group, i.e., R5 or R8, and the group containing the oxyalkylene segment, i.e., R6 or R9.

If desired, organosilicon compositions which are higher polymers containing more than x, y, and z units, and containing the same types of functionality as defined for the x, y, and z units, can be prepared according to the method of the invention.

Cyclosiloxanes used to prepare organosilicon compositions according to this invention include compositions having the formulae:

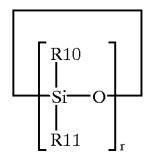 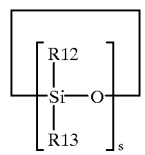

in which r and s represent an integer having a value of 3–10.

In the first cyclosiloxane composition of the formula:

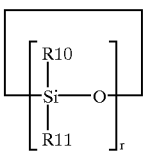

R10 and R11 can be any alkyl group containing 1–40 carbon atoms, preferably methyl, with the proviso that at least R10 or R11 is a higher carbon atom containing-group, i.e., a C5 or more, preferably a C8 or more group such as —(CH$_2$)$_7$CH$_3$, —(CH$_2$)$_{11}$CH$_3$, or —(CH$_2$)$_{15}$CH$_3$. The higher carbon atom containing group R10 or R11, therefore, should contain 5–40, preferably 8–40 carbon atoms. Representative cyclosiloxane compositions are 1,3,5,7-tetramethyl-1,3,5,7-tetra(1-octyl)cyclotetrasiloxane and 1,3,5,7-tetra(1-hexadecyl)-1,3,5,7-tetramethylcyclotetrasiloxane. In these compositions, r has a value of four.

If desired, R10 or R11 can also constitute an aryl group such as phenyl and xenyl (i.e., biphenyl); an aralkyl group such as benzyl, phenylethyl (i.e., phenethyl), and 2-phenylpropyl; an alkaryl group such as tolyl and xylyl; an haloalkyl group such as chloromethyl, 2-bromoethyl, 3-chloropropyl and 3,3,3-trifluoropropyl; an haloaryl group such as bromophenyl and chlorophenyl; an unsaturated alkenyl group such as vinyl, allyl, and hexenyl; or a substituted alkyl group such as acryloxypropyl, cyanopropyl, glycidoxypropyl, methacryloxypropyl, methoxypropyl, (methylthio)propyl, and ureidopropyl, for example; subject to the same proviso however, as noted above.

In the second cyclosiloxane composition of the formula:

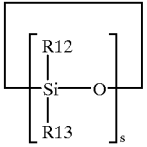

R12 can be any alkyl group containing 1–40 carbon atoms, preferably methyl, and R13 is a group containing an oxyalkylene segment represented by —C$_a$H$_{2a}$—O—(C$_2$H$_4$O)$_b$—(C$_3$H$_6$O)$_c$—Q.

If desired, R12 can also constitute an aryl group such as phenyl and xenyl (i.e., biphenyl); an aralkyl group such as benzyl, phenylethyl (i.e., phenethyl), and 2-phenylpropyl; an alkaryl group such as tolyl and xylyl; an haloalkyl group such as chloromethyl, 2-bromoethyl, 3-chloropropyl and 3,3,3-trifluoropropyl; an haloaryl group such as bromophenyl and chlorophenyl; an unsaturated alkenyl group such as vinyl, allyl, and hexenyl; or a substituted alkyl group such as acryloxypropyl, cyanopropyl, glycidoxypropyl, methacryloxypropyl, methoxypropyl, (methylthio)propyl, and ureidopropyl, for example.

Q is a terminating radical which can be an alkyl group of one to six carbon atoms, an aryl group such as phenyl, an aralkyl group such as benzyl, an alkaryl group such as tolyl, or a trialkylsilyl group such as the trimethylsilyl group —Si(CH$_3$)$_3$. The value of a is 2–8, b is 4–60, and c is 0–60. The oxyalkylene segment preferably has 50–99.9 mole percent of oxyethylene units —(C$_2$H$_4$O)$_b$, and 0.1–50 mole percent of oxypropylene units —(C$_3$H$_6$O)$_c$—. Preferably, terminating radical Q is a methyl group; and a is three whereby the group —C$_a$H$_{2a}$— is —(CH$_2$)$_3$—.

Representative cyclosiloxane compositions are 1,3,5,7-tetramethyl-1,3,5,7-tetra(1-propyl-3-oxy[polyethylene oxide(EO$_7$) methyl ether])cyclotetrasiloxane and 1,3,5,7-tetramethyl-1,3,5,7-tetra(1-propyl-3-oxy[polyethylene oxide(EO$_{12}$) methyl ether])cyclotetrasiloxane. In these compositions, the value of s is four. In the first composition, Q is methyl, a is 3, b is 7, and c is zero. In the second composition, Q is methyl, a is 3, b is 12, and c is zero.

It should be understood that while homopolymeric cyclosiloxanes such as shown above are preferred, copolymeric cyclosiloxanes, i.e., co-cyclic siloxanes, can also be used. Such copolymeric cyclosiloxane compositions are represented, for example, by the formulae:

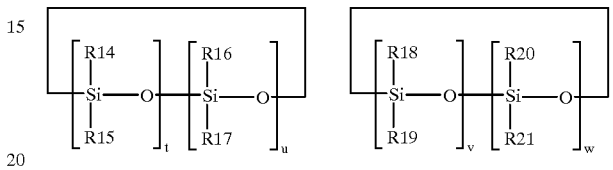

In these formulae, t, u, v, and w, each represent an integer having a value of 1–10, wherein the sum of t and u, and the sum of v and w, is greater than two.

In the first copolymeric cyclosiloxane composition of the formula:

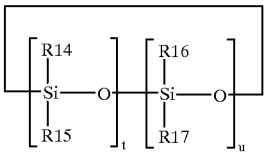

R14 to R17 can be any alkyl group containing 1–40 carbon atoms, preferably methyl, with the proviso that at least one of the groups R14 to R17 is a higher carbon atom containing group, i.e., a C5 or more, preferably a C8 or more group, such as —(CH$_2$)$_7$CH$_3$, —(CH$_2$)$_{11}$CH$_3$, or —(CH$_2$)$_{15}$CH$_3$. The higher carbon atom containing group, therefore, should contain 5–40, preferably 8–40 carbon atoms, while the remaining groups will generally all be methyl.

If desired, R14 to R17 can also constitute an aryl group such as phenyl and xenyl (i.e., biphenyl); an aralkyl group such as benzyl, phenylethyl (i.e., phenethyl), and 2-phenylpropyl; an alkaryl group such as tolyl and xylyl; an haloalkyl group such as chloromethyl, 2-bromoethyl, 3-chloropropyl and 3,3,3-trifluoropropyl; an haloaryl group such as bromophenyl and chlorophenyl; an unsaturated alkenyl group such as vinyl, allyl, and hexenyl; or a substituted alkyl group such as acryloxypropyl, cyanopropyl, glycidoxypropyl, methacryloxypropyl, methoxypropyl, (methylthio)propyl, and ureidopropyl, for example; subject to the same proviso however, as noted above.

In the second copolymeric cyclosiloxane composition of the formula:

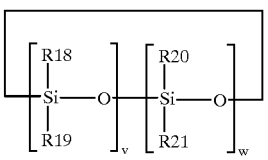

R18 to R21 can be any alkyl group containing 1–40 carbon atoms, preferably methyl, with the proviso that at least one of the groups R18 to R21 is a group containing an oxyalkylene segment represented by —$C_aH_{2a}$—O—$(C_2H_4O)_b$—$(C_3H_6O)_c$—Q.

If desired, R18 to R21 can also constitute an aryl group such as phenyl and xenyl (i.e., biphenyl); an aralkyl group such as benzyl, phenylethyl (i.e., phenethyl), and 2-phenylpropyl; an alkaryl group such as tolyl and xylyl; an haloalkyl group such as chloromethyl, 2-bromoethyl, 3-chloropropyl and 3,3,3-trifluoropropyl; an haloaryl group such as bromophenyl and chlorophenyl; an unsaturated alkenyl group such as vinyl, allyl, and hexenyl; or a substituted alkyl group such as acryloxypropyl, cyanopropyl, glycidoxypropyl, methacryloxypropyl, methoxypropyl, (methylthio)propyl, and ureidopropyl, for example; subject to the same proviso however, as noted above.

Q is a terminating radical which can be an alkyl group of one to six carbon atoms, an aryl group such as phenyl, an aralkyl group such as benzyl, an alkaryl group such as tolyl, or a trialkylsilyl group such as the trimethylsilyl group —$Si(CH_3)_3$. The value of a is 2–8, b is 4–60, and c is 0–60. The oxyalkylene segment preferably has 50–99.9 mole percent of oxyethylene units —$(C_2H_4O)_b$, and 0.1–50 mole percent of oxypropylene units —$(C_3H_6O)_c$—. Preferably, terminating radical Q is a methyl group; and a is three whereby the group —$C_aH_{2a}$— is —$(CH_2)_3$—. Except for the group containing the oxyalkylene segment, the remaining groups will generally all be methyl groups.

Such copolymeric cyclosiloxanes, i.e., co-cyclic siloxanes, are generally know in the art, and are described in, for example, U.S. Pat. No. 3,299,112 (Jan. 17, 1967) and U.S. Pat. No. 5,160,494 (Nov. 3, 1992).

An additional composition which can be included as a component in the ring opening polymerization reaction is a dimethylcyclosiloxane or a methylhydrogencyclosiloxane. Inclusion of this additional composition will reduce the amount of the other of the cyclosiloxanes compositions used in the reaction. This composition can be any one or a mixture of cyclic volatile methyl siloxanes such as hexamethylcyclotrisiloxane ($D_3$) a solid at room temperature with a boiling point of 134° C. and formula $\{(Me_2)SiO\}_3$; octamethylcyclotetrasiloxane ($D_4$) with a boiling point of 176° C., viscosity of 2.3 $mm^2/s$, and formula $\{(Me_2)SiO\}_4$; decamethylcyclopentasiloxane ($D_5$) with a boiling point of 210° C., viscosity of 3.87 $mm^2/s$, and formula $\{(Me_2)SiO\}_5$; dodecamethylcyclohexasiloxane ($D_6$) with a boiling point of 245° C., viscosity of 6.62 $mm^2/s$, and formula $\{(Me_2)SiO\}_6$; and the methylhydrogencyclosiloxane 1,3,5,7-tetramethylcyclotetrasiloxane of the formula $\{(MeH)SiO\}_4$.

Another composition which can be included as one of the components used in the ring opening polymerization reaction is a relatively short chain low molecular weight linear silicone endblocking composition. As it name implies, the inclusion of this composition in the reaction mixture enhances endblocking, i.e., trimethylsiloxy termination, for the organosilicon compositions prepared according to the method of the present invention. These relatively short chain low molecular weight linear silicone compositions generally have a structure corresponding to the formula $MD_eM$ wherein "e" can be from 0 to about 8; "M" represents a monofunctional unit $(CH_3)_3SiO_{1/2}$; and "D" represents a difunctional unit $(CH_3)_2SiO_{2/2}$. Some examples of relatively short chain low molecular weight linear silicone compositions which can be used are one or mixtures of compositions such as hexamethyldisiloxane (MM) with a boiling point of 100° C., viscosity of 0.65 $mm^2/s$, and formula $Me_3SiOSiMe_3$; octamethyltrisiloxane (MDM) with a boiling point of 152° C., viscosity of 1.04 $mm^2/s$, and formula $Me_3SiOMe_2SiOSiMe_3$; decamethyltetrasiloxane ($MD_2M$) with a boiling point of 194° C., viscosity of 1.53 $mm^2/s$, and formula $Me_3SiO(Me_2SiO)_2SiMe_3$; dodecamethylpentasiloxane ($MD_3M$) with a boiling point of 229° C., viscosity of 2.06 $mm^2/s$, and formula $Me_3SiO(Me_2SiO)_3SiMe_3$; tetradecamethylhexasiloxane ($MD_4M$) with a boiling point of 245° C., viscosity of 2.63 $mm^2/s$, and formula $Me_3SiO(Me_2SiO)_4SiMe_3$; and hexadecamethylheptasiloxane ($MD_5M$) with a boiling point of 270° C., viscosity of 3.24 $mm^2/s$, and formula $Me_3SiO(Me_2SiO)_5SiMe_3$. If desired, other linear methyl siloxanes can be used which have a viscosity of about 100 centistoke or less, preferably about 50 centistoke or less, and most preferably about 5 centistoke or less; in which case the value of "e" would be considerably in excess of 8, i.e., up to about 75.

The catalyst used in the method according to this invention can be any one of a wide variety of catalysts known in the art which are useful in reactions for the ring opening polymerization of cyclosiloxanes. Examples of some appropriate types of catalysts are alkali metal hydroxides, alkali metal alkoxides, alkali metal silanolates, sulfuric acid, hydrochloric acid, Lewis acids such as boron trifluoride and aluminum chloride, tetramethylammonium hydroxide, tetrabutylphosphonium silanolate, quaternary ammonium and phosphonium boron complexes, quaternary ammonium phosphates, quaternary ammonium borates, quaternary ammonium carbonates, quaternary ammonium silicates, trifluoromethane sulfonic acid (triflic acid), phosphonitrile halides (acidic phosphazenes), and phosphazene bases, which are described in U.S. Pat. No. 5,344,906 (Sep. 6, 1994); U.S. Pat. No. 5,670,596 (Sep. 23, 1997); U.S. Pat. No. 5,830,969 (Nov. 3, 1998); and U.S. Pat. No. 5,883,215 (Mar. 16, 1999).

As a particular example, some suitable alkali metal silanolates and alkali metal siloxanolates which can be used are sodium trimethylsilanolate $(CH_3)_3Si(ONa)$, sodium triphenylsilanolate $(C_6H_5)_3Si(ONa)$, disodium diphenylsilanolate $(C_6H_5)_2Si(ONa)_2$, disodium dimethylsilanolate $(CH_3)_2Si(ONa)_2$, disodium methylaminopropylsilanolate $(CH_3)[H_2NCH_2CH_2CH_2]Si(ONa)_2$, their potassium equivalents, dipotassium dimethylsilanolate $KO[(CH_3)_2SiO]K$, dipotassium dimethylsiloxanolate $KO[(CH_3)_2SiO]_nK$ where n is 4–8, dipotassium phenylmethylsilanolate $KO[(C_6H_5)(CH_3)SiO]K$, and dipotassium phenylmethylsiloxanolate $KO[(C_6H_5)(CH_3)SiO]_nK$ where n is 4–8.

Except for the presence of the particular cyclosiloxanes in the method of preparing organosilicon compositions according to this invention, the method employed herein is generally known in the prior art. Thus, U.S. Pat. No. 2.868,766 (Jan. 13, 1959), U.S. Pat. No. 2,994,684 (Aug. 1, 1961), and U.S. Pat. No. 3,002,951 (Oct. 3, 1961), all of which are assigned to the same assignee as the present invention, relate to methods of making various types of organosilicon compositions by polymerizing and copolymerizing cyclic type siloxane species at elevated temperatures, in the presence of a catalyst, for a time sufficient to obtain the desired state of polymerization to compositions of essentially linear construction, i.e., the ring opening polymerization mechanism.

As the method employed herein does not differ significantly from such methods, except for the presence of the particular cyclosiloxane compositions, reference may be had to these three US Patents for the general conditions needed to carry out the method. These patents are therefore considered incorporated herein by reference.

Thus, for example, polymerization of the cyclosiloxane compositions can be carried out at a temperature ranging from 30 to 250° C. for a time ranging from 5 minutes to three days. Generally, polymerization can be accelerated by increasing the reaction temperature.

The amount of the catalyst can be from about one alkali/acidic ion per 100 silicon atoms to one alkali/acidic ion per 200,000 silicon atoms. While polymerization can be achieved by using more or less than these amounts of an alkali/acid catalyst, this is not practical, as in the former case excessive amounts of acid/base would be required for neutralization of the catalyst at the end of the reaction, while in the latter case the use of only trace amounts of catalyst could hinder its effectiveness in the initial reaction.

While it is preferred to carry out the reaction in the absence of a solvent, the reaction can be conducted in the presence of solvents such as acetonitrile, dimethylformamide, decahydronaphthalene, toluene, p-chloro-toluene, o-dichloro-benzene, tetrahydrofuran, xylene, dimethyl sulfoxide, or dibutyl ether, if desired.

Any of the essential and optional components used in carrying out the polymerization reaction can be combined in stoichiometric quantities, or slight excess, necessary to achieve the desired distribution of repeating units in the polymer chain of the organosilicon composition. Thus, equivalent amounts of reactants should be employed in the process, although it may be necessary to use an excess of one or more of the reactants. The maximum amount is determined, for example, by economical considerations, as there is no benefit in employing an excess of a reactant that is not consumed. The minimum amount will depend on the type and purity of the reactants.

EXAMPLES

The following examples are set forth in order to illustrate this invention in more detail.
Alkyl Modified Siloxanes Example 1

A 100 ml round bottom flask was equipped with a magnetic stir bar, a thermometer, and a reflux condenser, and was charged with 2.1 g (0.6 mmoles) of 50 centistoke polydimethylsiloxane fluid, 31.9 g (107.5 mmoles) of octamethylcyclotetrasiloxane, and 11.0 g of 1,3,5,7-tetramethyl-1,3,5,7-tetra(1-octyl)cyclotetrasiloxane (16.0 mmoles). To this homogeneous mixture was added 0.045 g (0.1 weight percent) of trifluoromethanesulfonic acid (0.3 mmoles). The temperature was raised to and maintained at 75° C.±5° for 4 hours. Next, 3.0 g of sodium bicarbonate was added, and the mixture was allowed to cool to room temperature. After stirring for 2 hours at room temperature, the mixture was filtered to provide 41.4 g of clear viscous oil. This oil was characterized by $^{29}$Si and $^{13}$C NMR spectroscopy and GPC. The product mixture was found to contain 93% of a linear siloxane having a degree of polymerization (DP) of 700, i.e., the sum of x+y where z was zero. It contained 12.1 mole percent of pendant octyl groups.

Example 2

A 250 ml flask was equipped with a mechanical stirrer, thermometer, and a reflux condenser. To the flask was added 59.9 g (86.9 mmoles) of 1,3,5,7-tetramethyl-1,3,5,7-tetra(1-octyl)cyclotetrasiloxane, 33.1 g (112 mmoles) of octamethylcyclotetrasiloxane and 7.21 g (8.70 mmoles) of 5 centistoke polydimethylsiloxane fluid. To this homogeneous mixture was added 0.10 g (0.1 weight percent) of trifluoromethanesulfonic acid) (0.67 mmoles). The temperature was raised to and maintained at 75° C.±5° for 4 hours. Next, 5.0 g of sodium bicarbonate was added, and the mixture was allowed to cool to room temperature. After stirring for 2 hours at room temperature, the mixture was filtered to provide 93.2 g of a clear viscous oil. The oil was characterized by $^{29}$Si and $^{13}$C NMR spectroscopy and GPC. The product mixture was found to contain 86% of a linear siloxane with a DP of 76, i.e., the sum of x+y where z was zero. It contained 38.1 mole percent of pendant octyl groups.

Example 3

A 50 ml round bottom flask was equipped with a magnetic stir bar, a thermometer, a reflux condenser, and a gas inlet and outlet. The flask was charged with 0.8 g (0.93 mmoles) of 5 centistoke polydimethylsiloxane fluid, 15.0 g (50.6 mmoles) of octamethylcyclotetrasiloxane, and 15.0 g of 1,3,5,7-tetramethyl-1,3,5,7-tetra(1-octyl)cyclotetrasiloxane (21.8 mmoles). The mixture was heated to and maintained at 100° C.±5° for 1 hour, at which time the temperature was raised to 120° C.±5°. To the homogeneous reaction mixture was added 0.031 g (0.1 weight percent) of tetrabutylphosphonium silanolate. The temperature was maintained for 3 hours. Next, the temperature was raised to 170° C.±5 ° and held for 2 hours, and then the mixture was allowed to cool. After stirring for 2 hours at room temperature, the mixture was filtered to provide 28.3 g of clear viscous oil. The oil was characterized by $^{29}$Si and $^{13}$C NMR spectroscopy and GPC. The product mixture was found to contain 88% of a linear siloxane having a DP of 180, i.e., the sum of x+y where z was zero. It contained 25.3 mole percent of pendant octyl groups.

Example 4

A 250 ml flask was equipped with a mechanical stirrer, thermometer, and a reflux condenser. To the flask was added 57.1 g (50.1 mmoles) of 1,3,5,7-tetra(1-hexadecyl)-1,3,5,7-tetramethylcyclotetrasiloxane, 49.9 g (168 mmoles) of octamethylcyclotetrasiloxane, 2.46 g (10.2 mmoles) of 1,3,5,7-tetramethylcyclotetrasiloxane, and 7.76 g (9.36 mmoles) of 5 centistoke polydimethylsiloxane fluid. To this homogeneous mixture was added 0.117 g (0.1 weight percent) of trifluoromethanesulfonic acid) (0.78 mmoles). The temperature was raised to and maintained at 75° C.±5° for 4 hours. Next, 5.0 g of sodium bicarbonate was added, and the mixture was allowed to cool to room temperature. After stirring for 2 hours at room temperature, the mixture was filtered to provide 106 g of a clear viscous oil. The oil was characterized by $^{29}$Si and $^{13}$C NMR spectroscopy and GPC. The product mixture was found to contain 78% of a linear siloxane having a DP of 75, i.e., the sum of x+y where z was zero. It contained 14.9 mole percent of pendant hexadecyl groups and 3.9 mole percent of methyl hydrogen groups.
Polyether Modified Siloxanes Example 5

A 25 ml round bottom flask was equipped with a magnetic stir bar, a thermometer, a reflux condenser, and a gas inlet and outlet. The flask was charged with 0.76 g (0.92 mmoles) of 5 centistoke polydimethylsiloxane fluid, 10.6 g (35.7 mmoles) of octamethylcyclotetrasiloxane, and 5.00 g of 1,3,5,7-tetramethyl-1,3,5,7-tetra(1-propyl-3-oxy[polyethylene oxide(EO$_7$) methyl ether])cyclotetrasiloxane (2.84 mmoles). The mixture was heated to and maintained at 100° C.±5° for 1 hour, at which time the temperature was raised to 120° C.±5°. To the heterogeneous reaction mixture was added 0.016 g (0.12 mmoles, 0.1 weight percent) of potassium trimethylsilanolate. The temperature was maintained for 3 hours. Next, the temperature was lowered to 60° C.±5°, and approximately 0.024 g of $(CH_3)_3SiCl$, i.e., trimethylchlorosilane, (0.22 mmoles) was added in order to neutralize the silanolate catalyst. After mixing at 60° C.±5° for 2 hours, 2.0 g of sodium bicarbonate was added to neutralize the HCl generated during neutralization of the silanolate catalyst, and the mixture was allowed to cool. After stirring for 2 hours at room temperature, the mixture was filtered to provide 14.6 g of a clear viscous oil. The oil was characterized by $^{29}Si$ and $^{13}C$ NMR spectroscopy and GPC. The product mixture was found to contain 90% of a linear siloxane with a DP of 88, i.e., the sum of x+z where y was zero. It contained 13.1 mole percent of pendant polyether groups.

Example 6

A 50 ml round bottom flask was equipped with a magnetic stir bar, a thermometer, a reflux condenser, and a gas inlet and outlet. The flask was charged with 6.02 g (7.26 mmoles) of 5 centistoke polydimethylsiloxane fluid, and 21.3 g of 1,3,5,7-tetramethyl-1,3,5,7-tetra(1-propyl-3-oxy[polyethylene oxide($EO_{12}$) methyl ether])cyclotetrasiloxane (10.7 mmoles). The mixture was heated to and maintained at 100° C.±5° for 1 hour, at which time the temperature was raised to 120° C.±5°. To the heterogeneous reaction mixture was added 0.037 g (0.1 weight percent) of tetrabutylphosphonium silanolate. The temperature was maintained for 4 hours with stirring. Next, the temperature was raised to 170° C.±5° and held for 2 hours, and then the mixture was allowed to cool. After stirring for 2 hours at room temperature, the mixture was filtered to provide 24.8 g of clear viscous oil. The oil was characterized by $^{29}Si$ and $^{13}C$ NMR spectroscopy and GPC. The product mixture was found to contain 82% of a linear siloxane with a DP of 11, i.e., the sum of x+z where y was zero. It contained 23.3 mole percent pendant of polyether groups.

Example 7

A 50 ml round bottom flask was equipped with a magnetic stir bar, a thermometer, a reflux condenser, a gas inlet and outlet. The flask was charged with 1.01 g (1.22 mmoles) of a 5 centistoke polydimethylsiloxane fluid, 3.03 g (1.72 mmoles) of 1,3,5,7-tetramethyl-1,3,5,7-tetra(1-propyl-3-oxy[polyethylene oxide($EO_7$) methyl ether])cyclotetrasiloxane, 16.0 g (14.1 mmoles) of 1,3,5,7-tetra(1-hexadecyl)-1,3,5,7-tetramethylcyclotetrasiloxane, and 6.49 g (21.9 mmoles) of octamethylcyclotetrasiloxane. The mixture was heated to and maintained at 100° C.±5° for 1 hour, at which time the temperature was raised to 120° C.±5°. To the heterogeneous reaction mixture was added 0.027 g (0.1 weight percent) of tetrabutylphosphonium silanolate. The temperature was maintained for 4 hours with stirring. Next, the temperature was raised to 170° C.±5° and held for 2 hours, and then the mixture was allowed to cool. After stirring for 2 hours at room temperature, the mixture was filtered to provide 23.6 g of a clear viscous oil. The oil was characterized by $^{29}Si$ and $^{13}C$ NMR spectroscopy and GPC. The product mixture was found to contain 79% of a linear siloxane with a DP of 80, i.e., the sum of x+y+z and none of x, y, or z was zero. It contained 27.2 mole percent of pendant hexadecyl and 3.7 mole percent of pendant polyether groups.

While the organosilicon compositions described herein are useful in applications requiring any benefit attributed to organosilicon materials, these organosilicon compositions are primarily intended for use in personal care. Thus, they can be used alone or combined with cosmetic ingredients to form a number of over-the-counter (OTC) personal care products. For example, they are useful as carriers or emulsifiers in antiperspirants and deodorants. They are lubricious and can improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, and shaving lathers. They can be used in hair shampoos, hair conditioners, hair sprays, mousses, permanents, depilatories, and cuticle coats, to enhance gloss, as emulsifiers, and/or to provide conditioning benefits.

In cosmetics, they can be effective emulsifiers, or function as leveling and spreading agents for pigments in make-ups, color cosmetics, foundations, blushes, lipsticks, lip balms, eyeliners, mascaras, oil removers, color cosmetic removers, and powders. When incorporated into sticks, gels, lotions, aerosols, and roll-ons, they can impart a dry and silky-smooth feel.

These organosilicon compositions are also capable of functioning as carriers or emulsifiers for pharmaceuticals, biocides, herbicides, pesticides, and other biologically active substances; and they have utility as additives for cellulose or synthetic nonwoven carrier substrates used in wet-like cleansing wipes such as wet-wipes, tissues, and towels, marketed generally for personal hygiene and household cleaning tasks.

These organosilicon compositions are linear in structure, which is defined according to this invention as being a structure containing monofunctional "M" units $(CH_3)_3SiO_{1/2}$ and difunctional "D" units $(CH_3)_2SiO_{2/2}$. The organosilicon compositions are not believed to contain any significant portion of trifunctional "T" units $CH_3SiO_{3/2}$ or tetrafunctional "Q" units $SiO_{4/2}$.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A method of preparing an organosilicon composition comprising heating in the absence of a solvent a mixture of (i) a dimethylcyclosiloxane, (ii) a cyclosiloxane containing a C5 or more carbon atom containing group, and (iii) a cyclosiloxane containing an oxyalkylene segment, in the presence of a catalyst, at a temperature and for a time sufficient to cause polymerization of cyclosiloxanes (i) to (iii).

2. A method according to claim 1 in which the mixture further includes (iv) a short chain low molecular weight linear silicone composition having the structure $MD_eM$ wherein e is 0 to about 75, M represents a monofunctional unit $(CH_3)_3SiO_{1/2}$, and D represents a difunctional unit $(CH_3)_2SiO_{2/2}$.

3. A method according to claim 1 in which the catalyst is selected from the group consisting of alkali metal hydroxides, alkali metal alkoxides, alkali metal silanolates, sulfuric acid, hydrochloric acid, Lewis acids, tetramethylammonium hydroxide, tetrabutylphosphonium silanolate, quaternary ammonium and phosphonium boron complexes, quaternary ammonium phosphates, quaternary ammonium borates, quaternary ammonium carbonates, quaternary ammonium silicates, trifluoromethane sulfonic acid (triflic acid), phosphonitrile halides (acidic phosphazenes), and phosphazene bases.

4. A method according to claim 1 in which the cyclosiloxane containing a C5 or more carbon atom containing group has a structure corresponding to the formula:

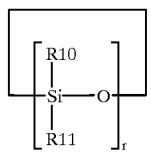

in which R10 and R11 are alkyl groups containing 1–40 carbon atoms with the proviso that at least one of R10 or R11 is a C5 or more carbon atom containing group, and r is 3 to 10.

5. A method according to claim 1 in which the cyclosiloxane containing the oxyalkylene segment has a structure corresponding to the formula:

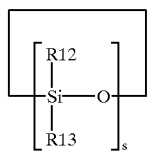

in which R12 is an alkyl group containing 1–40 carbon atoms, and R13 is a group containing an oxyalkylene segment represented by $-C_aH_{2a}-O-(C_2H_4O)_b-(C_3H_6O)_c-Q$ in which Q is a terminating radical selected from the group consisting of an alkyl group of one to six carbon atoms, an aryl group, an aralkyl group, an alkaryl group, and a trialkylsilyl group, a is 2–8, b is 4–60, c is 0–6, the oxyalkylene segment containing 50–99.9 mole percent of oxyethylene units $-(C_2H_4O)_b$, and 0.1–50 mole percent of oxypropylene units $-(C_3H_6O)_c-$, and s is 3–10.

6. A method of preparing an organosilicon composition comprising heating in the absence of a solvent a mixture of (i) a dimethylcyclosiloxane or a methylhydrogencyclosiloxane, and (ii) a copolymeric cyclosiloxane containing a C5 or more carbon atom containing group, in the presence of a catalyst, at a temperature and for a time sufficient to cause polymerization of cyclosiloxanes (i) and (ii), the copolymeric cyclosiloxane containing the C5 or more carbon atom containing group having a structure corresponding to the formula:

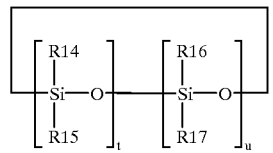

in which R14 to R17 are alkyl groups containing 1–40 carbon atoms, with the proviso that at least one of the groups R14 to R17 is a C5 or more carbon atom containing group, and t and u each have a value of 1 to 10 wherein the sum of t and u is greater than two.

7. A method according to claim 6 in which the mixture further includes (iv) a short chain low molecular weight linear silicone composition having the structure $MD_eM$ wherein e is 0 to about 75, M represents a monofunctional unit $(CH_3)_3SiO_{1/2}$, and D represents a difunctional unit $(CH_3)_2SiO_{2/2}$.

8. A method of preparing an organosilicon composition comprising heating in the absence of a solvent a mixture of (i) a dimethylcyclosiloxane, and (ii) a copolymeric cyclosiloxane containing an oxyalkylene segment, in the presence of a catalyst, at a temperature and for a time sufficient to cause polymerization of cyclosiloxanes (i) and (ii), the copolymeric cyclosiloxane containing the oxyalkylene segment having a structure corresponding to the formula:

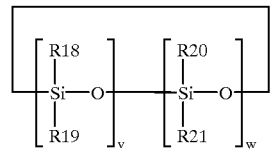

in which R18 to R21 are alkyl group containing 1–40 carbon atoms, with the proviso that at least one of the groups R18 to R21 is a group containing an oxyalkylene segment represented by $-C_aH_{2a}-O-(C_2H_4O)_b-(C_3H_6O)_c-Q$ in which Q is a terminating radical selected from the group consisting of an alkyl group of one to six carbon atoms, an aryl group, an aralkyl group, an alkaryl group, and a trialkylsilyl group, a is 2–8, b is 4–60, c is 0–60, the oxyalkylene segment having 50–99.9 mole percent of oxyethylene units $-(C_2H_4O)_b$, and 0.1–50 mole percent of oxypropylene units $-(C_3H_6O)_c-$, and v and w each have a value of 1 to 10 wherein the sum of v and w is greater than two.

9. A method according to claim 8 in which the mixture further includes (iv) a short chain low molecular weight linear silicone composition having the structure $MD_eM$ wherein e is 0 to about 75, M represents a monofunctional unit $(CH_3)_3SiO_{1/2}$, and D represents a difunctional unit $(CH_3)_2SiO_{2/2}$.

10. A method of preparing an organosilicon composition comprising heating in the absence of a solvent a mixture of (i) a dimethylcyclosiloxane (ii) a copolymeric cyclosiloxane containing a C5 or more carbon atom containing group, and (iii) a copolymeric cyclosiloxane containing an oxyalkylene segment, in the presence of a catalyst, at a temperature and for a time sufficient to cause polymerization of cyclosiloxanes (i) to (iii), the copolymeric cyclosiloxane containing the C5 or more carbon atom containing group having a structure corresponding to the formula:

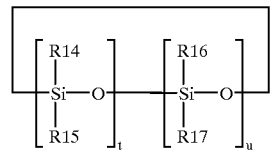

in which R14 to R17 are alkyl groups containing 1–40 carbon atoms, with the proviso that at least one of the groups R14 to R17 is a C5 or more carbon atom containing group, t and u each have a value of 1 to 10 wherein the sum of t and u is greater than two, the copolymeric cyclosiloxane containing the oxyalkylene segment having a structure corresponding to the formula:

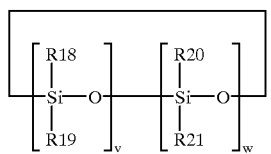

in which R18 to R21 are alkyl group containing 1–40 carbon atoms, with the proviso that at least one of the groups R18 to R21 is a group containing an oxyalkylene segment represented by —$C_aH_{2a}$—O—$(C_2H_4O)_b$—$(C_3H_6O)_c$—Q in which Q is a terminating radical selected from the group consisting of an alkyl group of one to six carbon atoms, an aryl group, an aralkyl group, an alkaryl group, and a trialkylsilyl group, a is 2–8, b is 4–60, c is 0–60, the oxyalkylene segment having 50–99.9 mole percent of oxyethylene units —$(C_2H_4O)_b$, and 0.1–50 mole percent of oxypropylene units —$(C_3H_6O)_c$—, and v and w each have a value of 1 to 10 wherein the sum of v and w is greater than two.

11. A method according to claim 10 in which the mixture further includes (iv) a short chain low molecular weight linear silicone composition having the structure $MD_eM$ wherein e is 0 to about 75, M represents a monofunctional unit $(CH_3)_3SiO_{1/2}$, and D represents a difunctional unit $(CH_3)_2SiO_{2/2}$.

12. A method of preparing an organosilicon composition comprising heating in the absence of a solvent a mixture of (i) a methylhydrogencyclosiloxane and (ii) a cyclosiloxane containing a C5 or more carbon atom containing group, in the presence of a catalyst, at a temperature and for a time sufficient to cause polymerization of cyclosiloxanes (i) and (ii).

13. A method of preparing an organosilicon composition comprising heating a mixture of (i) a methylhydrogencyclosiloxane and (ii) a cyclosiloxane containing an oxyalkylene segment, in the presence of a catalyst, at a temperature and for a time sufficient to cause polymerization of cyclosiloxanes (i) and (ii).

* * * * *